United States Patent [19]
Shieh

[11] Patent Number: 5,861,584
[45] Date of Patent: Jan. 19, 1999

[54] STETHOSCOPE

[76] Inventor: Woei-Kang Shieh, No. 63, Yung-Ping Street, Lu-Chu, Taipei Hsien, Taiwan

[21] Appl. No.: 942,429

[22] Filed: Oct. 1, 1997

[51] Int. Cl.$^6$ ...................................................... A61B 7/02
[52] U.S. Cl. ........................................... 181/131; 181/137
[58] Field of Search .................................... 181/131, 137; 381/67

[56] References Cited

U.S. PATENT DOCUMENTS

| | | | |
|---|---|---|---|
| 832,032 | 10/1906 | Borden | 181/131 |
| 4,928,786 | 5/1990 | Allen | 181/137 |
| 5,514,840 | 5/1996 | Selinger | 181/131 |

*Primary Examiner*—Khanh Dang
*Attorney, Agent, or Firm*—Townsend and Townsend and Crew LLP

[57] ABSTRACT

A stethoscope includes a chestpiece with at least one sound gathering device, a binaural assembly with two earpieces, and a sound transmission unit between the chestpiece and the binaural assembly for transmitting auscultatory sounds from the chestpiece to the earpieces. The chestpiece confines an acoustic path therein. The sound gathering device is mounted on the chestpiece in acoustic communication with the acoustic path. The sound transmission unit includes a rigid first hollow connector which has a first end mounted on the chestpiece in acoustic communication with the acoustic path and a second end formed as a tubular wall, and a flexible second hollow connector. The second hollow connector has a sleeve portion and a pair of transmission tubes connected integrally at one end to the sleeve portion and mated with the earpieces at an opposite end. The sleeve portion is sleeved over the tubular wall and engages sealingly the latter.

7 Claims, 5 Drawing Sheets

STETHOSCOPE

BACKGROUND OF THE INVENTION

1. Field of the Invention

The invention relates to a stethoscope, more particularly to a stethoscope which has a simplified structure so as to facilitate the assembly thereof.

2. Description of the Related Art

Referring to FIG. 1, a conventional stethoscope 70 is shown to include a chestpiece 73, a binaural assembly (not shown) consisting of two earpieces, and sound transmission means interposed between the chestpiece 73 and the binaural assembly (not shown). The chestpiece 73 is adapted to be placed against a body of a person for gathering auscultatory sounds therefrom.

As illustrated, the chestpiece 73 includes a chestpiece body 73A which confines an acoustic path 73B therein, and two sound gathering devices 74, 75 mounted at two opposite ends of the chestpiece body 73A and in acoustic communication with the acoustic path 73B. The sound transmission means is capable of transmitting the auscultatory sounds from the chestpiece to the earpieces, and includes a rigid first connector 72 which has a first end 723 mounted on the chestpiece body 73A at a radial opening 731 in the latter such that the first connector 72 is in acoustic communication with the acoustic path 73B, and a second end 721 formed as a tubular wall 722 of an 8-shaped cross section. The sound transmission means further includes a rigid second connector 71 which has an intermediate 8-shaped section 711 mounted sealingly in the tubular wall 722 such that a rear section 712 thereof extends within the first rigid connector 72 while a front section of the second connector 71 constituted by a pair of insert tube 723 is exposed outwardly of the first rigid connector 72. A pair of rubber tubings 76 has two first portions sleeved sealingly and frictionally on the insert tubes 723, and two second portions connected to the earpieces of the binaural assembly.

A drawback of the conventional stethoscope resides in that the sound transmission means employed therein includes many components, the structure of which are relatively complicated, thereby prolonging the assembly time and inconveniences during assembly. In addition, the possibility of sound loss is relatively high.

SUMMARY OF THE INVENTION

The object of this invention is to provide a stethoscope which includes sound transmission means of simplified structure so as to facilitate the assembly thereof and minimize the possibility of sound loss.

Accordingly, the stethoscope of this invention includes a chestpiece with at least one sound gathering device, a binaural assembly with two earpieces, and sound transmission means between the chestpiece and the binaural assembly for transmitting auscultatory sounds from the chestpiece to the earpieces. The chestpiece is adapted to be placed against a body of a subject for gathering the auscultatory sounds therefrom, and includes a chestpiece body which confines an acoustic path. The sound gathering device is mounted on the chestpiece body in acoustic communication with the acoustic path. The sound transmission means includes a rigid first hollow connector which has a first end mounted on the chestpiece body in acoustic communication with the acoustic path and a second end formed as a tubular wall, and a flexible second hollow connector. The second hollow connector has a sleeve portion and a pair of transmission tubes connected integrally at one end to the sleeve portion and mated with the earpieces at an opposite end. The sleeve portion is sleeved over the tubular wall and engages sealingly the latter.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
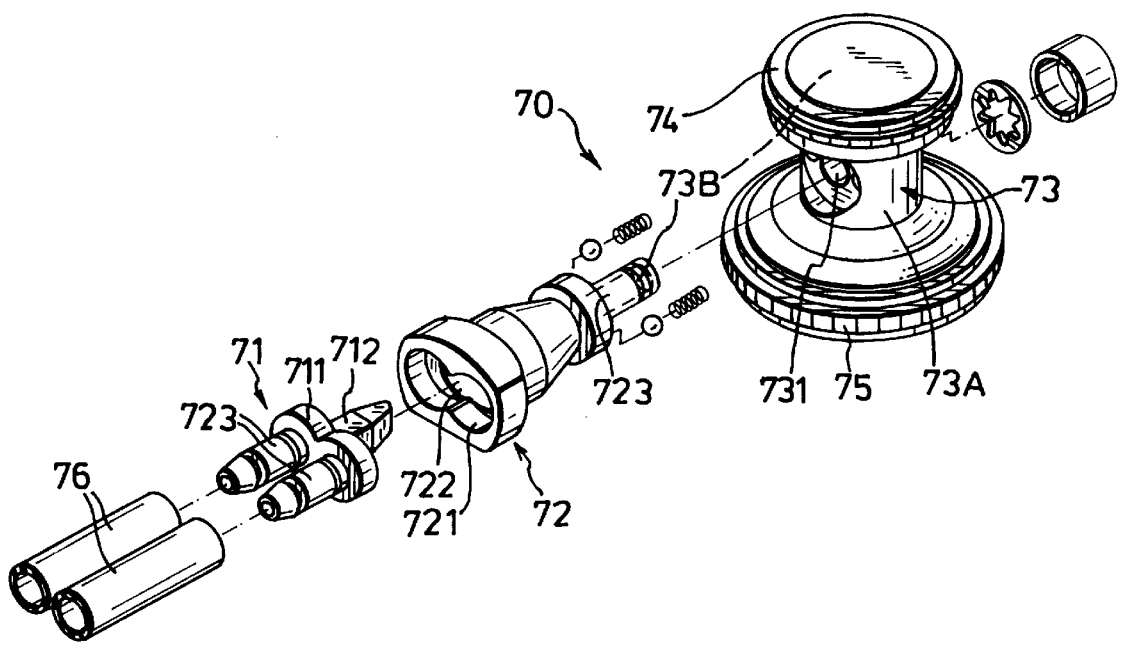
FIG. 1 is a fragmentary exploded view of a conventional stethoscope.
Figure 2:
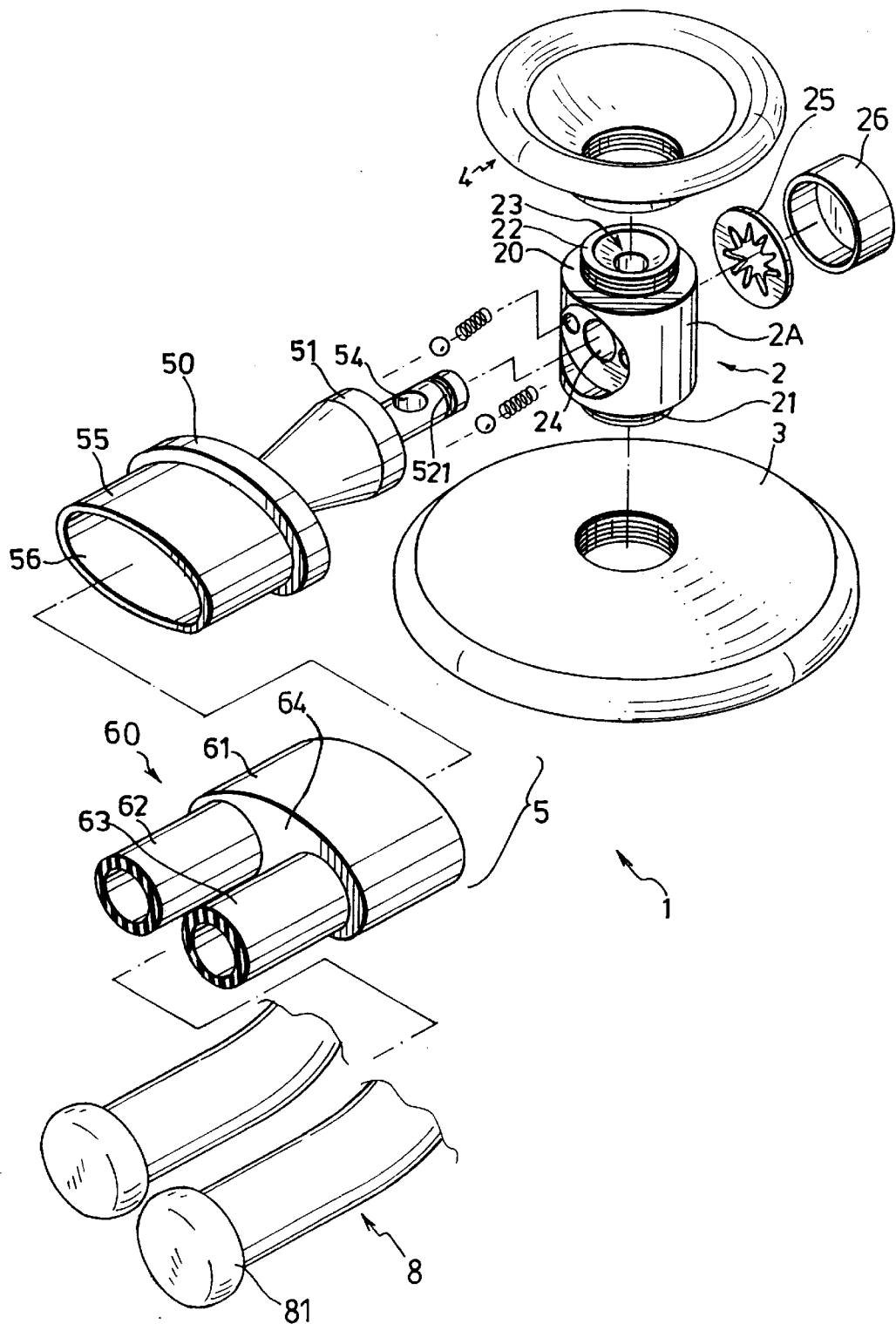
FIG. 2 is a fragmentary exploded view of a preferred embodiment of a stethoscope of this invention.
Figure 3:
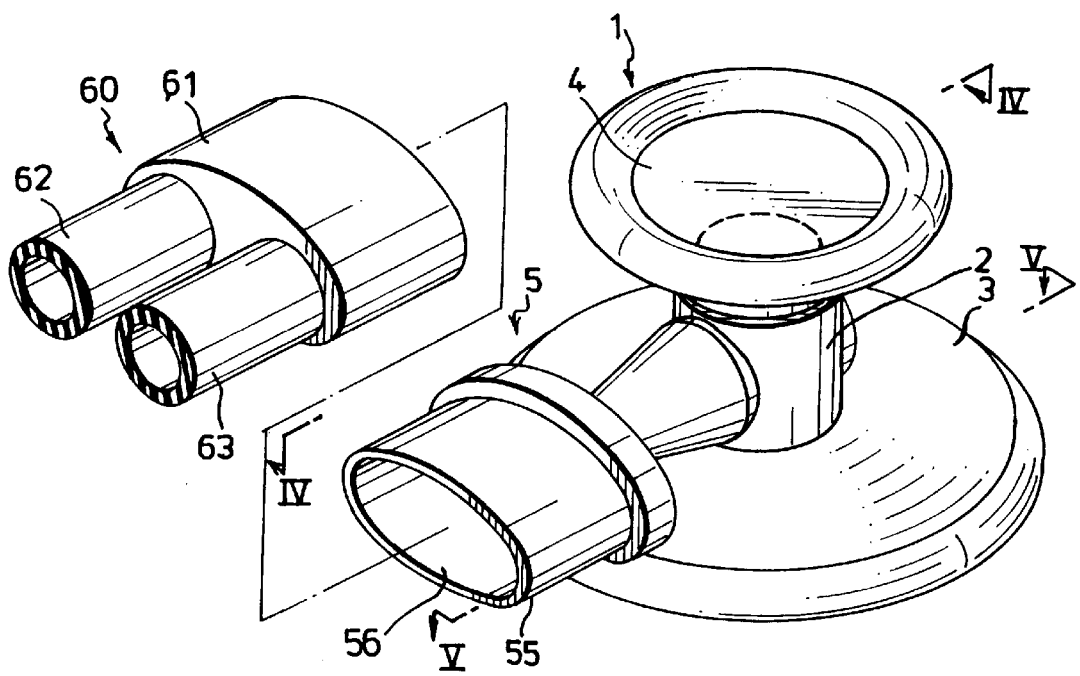
FIG. 3 illustrates how one part of a sound transmission means of the preferred embodiment is connected to a chestpiece.

Referring to FIGS. 2 and 3, the preferred embodiment of a stethoscope of this invention is shown to include a chestpiece 2, a binaural assembly 8 and a sound transmission unit 5.

The chestpiece 2 is adapted to be placed against a body of a subject for gathering auscultatory sounds therefrom. As illustrated, the chestpiece 2 is conventional in connection and includes a cylindrical chestpiece body 2A which confines an axially extending acoustic path 23. Two sound gathering devices 3, 4 are mounted on the chestpiece body 2A at two opposed ends 21, 22 of the latter and are in acoustic communication with the acoustic path 23. The sound gathering devices are capable of gathering low frequency auscultatory sounds and high frequency auscultatory sounds, respectively.

The binaural assembly 8 is conventional in connection and includes two earpieces 81.

Figure 4:
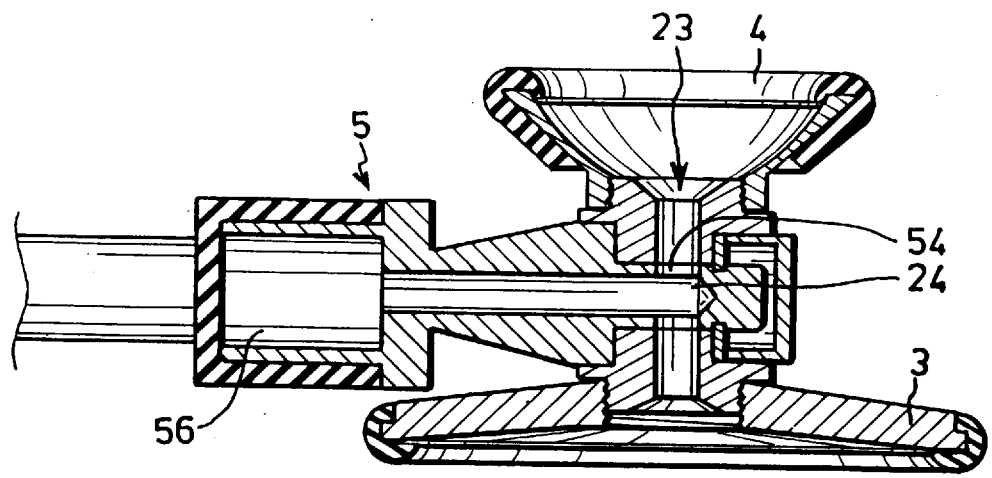
FIG. 4 is a partly sectional side view of the preferred embodiment taken along lines IV—IV of FIG. 3.

The sound transmission unit 5 is disposed between the chestpiece 2 and the binaural assembly 8 for transmitting the auscultatory sounds from the chestpiece 2 to the earpieces 81. The sound transmission unit 5 includes a rigid first hollow connector 50 and a flexible second hollow connector 60. The first connector 50 is made of metal and defines an axial sound passage 56 therethrough. The first connector 50 has a first end 51 mounted on the chestpiece body 2A at a radial hole 24 in the latter such that the acoustic path 23 is in acoustic communication with the sound passage 56 via a radial hole 54 in the front end 51 (see FIG. 4). The connection between the first connector 50 and the chestpiece body 2A is conventional and will not be detailed further. The second end of the first connector 50 is formed as a tubular wall 55 or a tubular joint portion. The second connector 60 is made of rubber, and has a sleeve portion 61 formed as a single tubular wall, and a pair of transmission tubes 62, 63 connected integrally at one end wall to the sleeve portion 61 and mated with the earpieces 81 at an opposite end. The sleeve portion 61 embraces the tubular wall 55 and engages sealingly and frictionally the latter. The end wall 64 extends transversely and outwardly of the tubular wall 55. The transmission tubes 62, 63 extend from the end wall 64.

Figure 5:
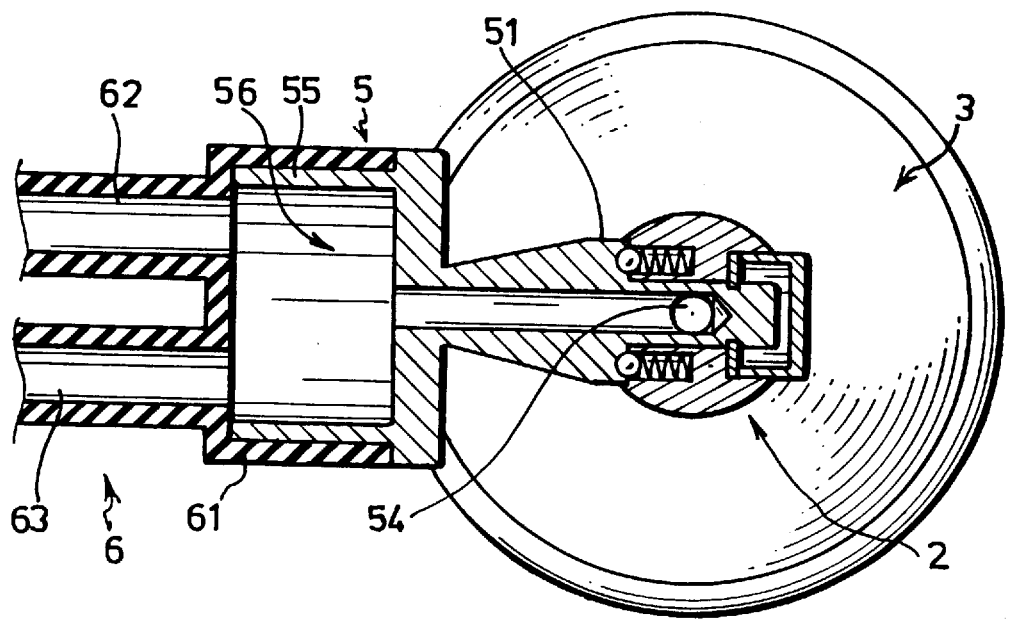
FIG. 5 is a partly sectional top view of the preferred embodiment taken along lines V—V of FIG. 3.

In the preferred embodiment, a retainer 25 (see FIG. 2) engages an annular groove 521 in the first end 51 of the first connector 50 so as to prevent disengagement of the first connector 50 from the chestpiece body 2A. A pair of spring-loaded balls are disposed between the chestpiece body 2A and the first connector 50 to reinforce the connection therebetween (see FIG. 5). A cap 26 (see FIG. 2) is sleeved around the protruding section of the first end of the first connector 50 to enhance the appearance of the stethoscope (see FIG. 4).

Figure 6:
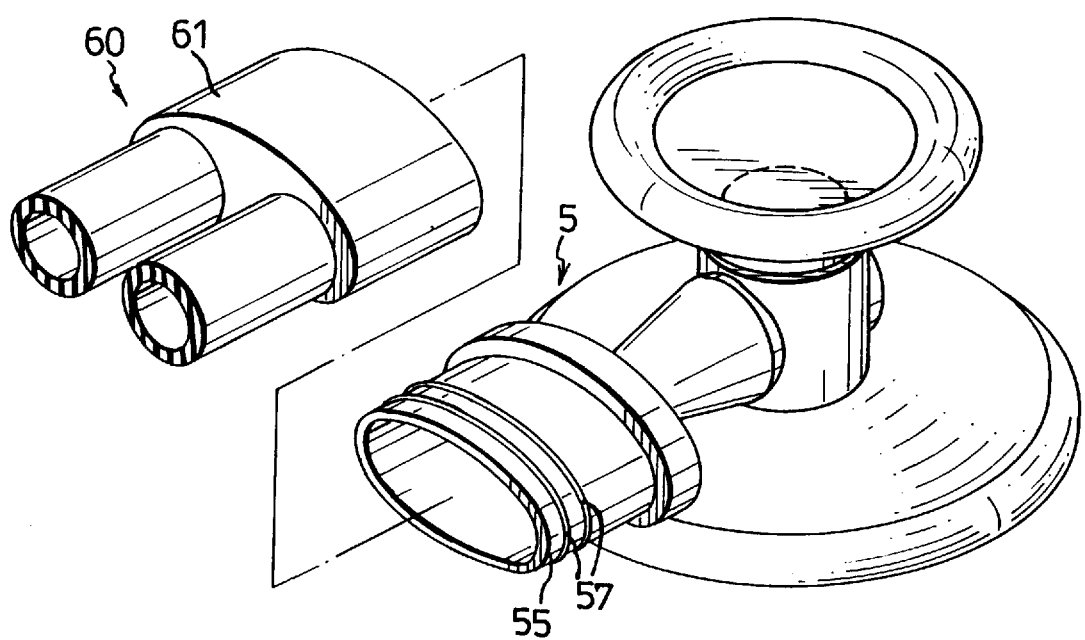
FIG. 6 is a fragmentary exploded view of a modified preferred embodiment of this invention.

Referring to FIG. 6, in a modified preferred embodiment, the tubular wall 55 of the first connector 5 has a ribbed external surface 57 for engaging tightly the sleeve portion 61 of the second connector 60. The features are the same as the previous embodiment.

Therefore, unlike the aforementioned prior art, which teaches the use of a rigid second connector 71 for connecting rubber tubings 76 to a rigid connector 72, the sleeve portion 61 of the second connector 60, which has transmission tubes 62, 63 connected integrally thereto, is mounted directly on the tubular wall 55 of the first connector 50. As a result, connection of the second connector 60 to the first connector 50 can be accomplished in a single step, and the possibility of sound loss can be minimized.

With this invention thus explained, it is apparent that numerous modifications and variations can be made without departing from the scope and spirit of this invention. It is therefore intended that this invention be limited only as indicated in the appended claims.

I claim:

1. A stethoscope, comprising:
   a chestpiece adapted to be placed against a body of a subject for gathering auscultatory sounds therefrom, said chestpiece including a chestpiece body which confines an acoustic path, and at least one sound gathering device mounted on said chestpiece body and in acoustic communication with said acoustic path;
   a binaural assembly including two earpieces; and
   sound transmission means for transmitting the auscultatory sounds from said chestpiece to said earpieces, said sound transmission means including
      a metallic first hollow connector having a first end mounted on said chestpiece body and in acoustical communication with said acoustic path, and a second end formed as a tubular wall; and
      a non-metallic second hollow connector having a sleeve portion with an open end for receiving said tubular wall and an end wall opposite to said open end, said second hollow connector further having a pair of flexible transmission tubes extending axially and integrally from said end wall and concurrently communicated with an interior passage of said sleeve portion and said acoustic path, said transmission tubes extending to said earpieces, said sleeve portion being sleeved over said tubular wall and engaging sealingly said tubular wall.

2. A stethoscope as defined in claim 1, wherein said tubular wall has a ribbed external surface for engaging tightly said sleeve portion.

3. A stethoscope as defined in claim 1, wherein said first hollow connector is made of metal and said second hollow connector is made of rubber, whereby said sleeve portion is frictionally retained on said tubular wall.

4. A stethoscope as defined in claim 1, wherein said chestpiece body has two of said sound gathering devices mounted thereon for gathering high frequency auscultatory sounds and low frequency auscultatory sounds, respectively.

5. A stethoscope, comprising:
   a chestpiece adapted to be placed against a body of a subject for gathering auscultatory sounds therefrom, said chestpiece including a chestpiece body which confines an acoustic path, and at least one sound gathering device mounted on said chestpiece body and in acoustic communication with said acoustic path;
   a sound transmission unit including
      a first hollow connector which is made of a rigid material and which has first and second ends, and a sound passage extending between said first and second ends, said first end being structurally and acoustically connected to said chest body, said second end being configured to be a tubular joint portion; and
      a second hollow connector which has a single tubular wall to embrace fixedly said tubular joint portion, said single tubular wall having an integral end wall extending transversely and outwardly of said tubular portion, said second hollow connector further having two flexible transmission tubes which are structurally connected to said end wall and which are acoustically communicated with said sound passage.

6. A stethoscope as defined in claim 5, wherein said tubular joint portion has a ribbed external surface for engaging tightly said single tubular wall.

7. A stethoscope as defined in claim 5, wherein said first hollow connector is made of metal and said second hollow connector is made of a flexible material as an integral piece which includes said single tubular wall and said flexible transmission tubes.

* * * * *